United States Patent
Ou Yang et al.

(10) Patent No.: US 12,253,415 B2
(45) Date of Patent: Mar. 18, 2025

(54) NON-CONTACT BODY TEMPERATURE MEASURING DEVICE AND METHOD THEREOF

(71) Applicant: AViTA Corporation, New Taipei (TW)

(72) Inventors: Hsing Ou Yang, New Taipei (TW); Hsuan-Hao Shih, New Taipei (TW); Ta-Chieh Yang, New Taipei (TW); Chih-Yuan Huang, New Taipei (TW)

(73) Assignee: AViTA Corporation, New Taipei (TW)

( * ) Notice: Subject to any disclaimer, the term of this patent is extended or adjusted under 35 U.S.C. 154(b) by 499 days.

(21) Appl. No.: 17/492,666

(22) Filed: Oct. 3, 2021

(65) Prior Publication Data
US 2023/0105817 A1 Apr. 6, 2023

(30) Foreign Application Priority Data
Oct. 15, 2020 (TW) ................. 109135768

(51) Int. Cl.
*G01J 5/00* (2022.01)
*G01S 13/42* (2006.01)
(Continued)

(52) U.S. Cl.
CPC ............. *G01J 5/0025* (2013.01); *G01S 13/42* (2013.01); *G01S 13/58* (2013.01); *G01J 5/0265* (2013.01)

(58) Field of Classification Search
None
See application file for complete search history.

(56) References Cited

U.S. PATENT DOCUMENTS

| 2011/0118608 A1* | 5/2011 | Lindner | G01J 5/0846 600/474 |
| 2013/0096437 A1* | 4/2013 | Weng | G01J 5/0022 600/474 |

(Continued)

FOREIGN PATENT DOCUMENTS

| CN | 2593285 | 12/2003 |
| CN | 204301867 | 4/2015 |

(Continued)

OTHER PUBLICATIONS

Guanghao Sun, Shigeto Abe, Osamu Takei and Takemi Matsui, A Portable screening system for onboard entry screening at international airports using a microwave radar, reflective photo sensor and thermography, 2011 2nd International Conference on Instrumentation, Communication, Information Technology and Biomedical Engineering Nov. 8-9, 2011, Bandung Indonesia IEEE, Piscataway, NJ, Nov. 8, 2011 (Nov. 8, 2011), p. 107-110.

(Continued)

*Primary Examiner* — Erica S Lin
(74) *Attorney, Agent, or Firm* — Ying-Ting Chen

(57) ABSTRACT

A non-contact body temperature measuring device includes a temperature measuring unit, a Doppler radar, a processing unit, and a display unit. The temperature measuring unit measures a temperature of a human body in a non-contact manner. The Doppler radar emits radar waves to the human body and receives reflected radar waves. The processing unit, which is electrically connected to the temperature measuring unit and the Doppler radar, determines measurement spots on the human body based on the reflected radar waves, controls the temperature measuring unit to measure temperatures of the measurement spots, and generates a body temperature measuring value based on the temperatures of the measurement spots. The display unit is electri- (Continued)

cally connected to the processing unit for displaying the body temperature measuring value.

15 Claims, 3 Drawing Sheets

(51) Int. Cl.
  *G01S 13/58* (2006.01)
  *G01J 5/02* (2022.01)

(56) References Cited

U.S. PATENT DOCUMENTS

| | | | |
|---|---|---|---|
| 2016/0049108 A1* | 2/2016 | Yajima | A63F 13/5255 345/212 |
| 2016/0313442 A1 | 10/2016 | Ho et al. | |
| 2017/0035302 A1 | 2/2017 | Mullin et al. | |

FOREIGN PATENT DOCUMENTS

| | | |
|---|---|---|
| CN | 106999060 | 8/2017 |
| CN | 109974862 | 7/2019 |
| CN | 110888121 | 3/2020 |
| TW | M562965 | 7/2018 |
| TW | 201913052 | 4/2019 |
| WO | WO2012067282 | 5/2012 |
| WO | WO2020128150 | 6/2020 |

OTHER PUBLICATIONS

Poornima G R et al., Surveillanace radio detection and ranging with thermal imaging camera, 2017 2nd IEEE International Conference on Recent Trends in Electronics, Information & Communication Technology (RTEICT), May 19-20, 2017, India, pp. 2057-2060.

* cited by examiner

NON-CONTACT BODY TEMPERATURE MEASURING DEVICE AND METHOD THEREOF

BACKGROUND OF THE PRESENT INVENTION

Field of Invention

The present invention relates to a non-contact body temperature measuring device, and more particularly to a non-contact body temperature measuring device and method thereof with improved measurement accuracy.

Description of Related Arts

Generally speaking, a forehead thermometer is used to measure the forehead temperature of a human body in a non-contact manner. In order to improve measurement accuracy, the conventional forehead thermometer is installed with an infrared distance measuring device to measure a distance between the forehead thermometer and a user to be measured, so as to ensure that the user is not too far away from the forehead thermometer during the process of measuring the forehead temperature. However, during the process of measuring the forehead temperature, the measurement angle may be shifted due to the hand shaking of the holder, that adversely affect the accuracy of the measurement result. As a result, the infrared distance measuring device of the conventional forehead thermometer only measures the distance between the forehead thermometer and the user to be measured but is unable to determine the measurement angle of the forehead thermometer.

SUMMARY OF THE PRESENT INVENTION

An objective of the present invention is to provide a non-contact body temperature measuring device and method thereof which can obtain a body temperature measuring value with higher accuracy and solve the conventional technology problems.

Another objective of the present invention is to provide a non-contact body temperature measuring device and method thereof for measuring a temperature of a human body in a non-contact manner by measuring temperatures of a plurality of measurement spots and generating a body temperature measuring value based on the temperatures of the plurality of measurement spots.

Another objective of the present invention is to provide a non-contact body temperature measuring device and method thereof for generating the body temperature measuring value based on an average value and a highest value of the temperatures of the plurality of measurement spots.

In order to achieve the objective, the present invention provides a non-contact body temperature measuring device including a temperature measuring unit, a Doppler radar, a processing unit, and a display unit. The temperature measuring unit is configured to measure a temperature of a human body in a non-contact manner. The Doppler radar is configured to emit a plurality of radar waves to a human body and receive reflected radar waves from the human body. The processing unit is electrically connected to the temperature measuring unit and the Doppler radar and configured to determine a plurality of measurement spots on the human body based on the reflected radar waves, control the temperature measuring unit to measure temperatures of the plurality of measurement spots, and generate a body temperature measuring value based on the temperatures of the plurality of measurement spots. The display unit is electrically connected to the processing unit and configured to display the body temperature measuring value.

According to one embodiment of the non-contact body temperature measuring device of the present invention, the temperature measuring unit can be an infrared temperature measuring unit.

According to one embodiment of the non-contact body temperature measuring device of the present invention, the processing unit is configured to obtain relative angles and relative distances between a plurality of locations on the human body and the Doppler radar based on the reflected radar waves reflected from the plurality of locations on the human body, and determine the plurality of measurement spots on the human body based on relative angles and relative distances between the plurality of locations and the Doppler radar.

According to one embodiment of the non-contact body temperature measuring device of the present invention, the processing unit is configured to obtain a relative velocity between the human body and the Doppler radar based on the reflected radar waves, wherein when the relative velocity is within a predetermined velocity range, the processing unit generates the body temperature measuring value based on the temperatures of the plurality of measurement spots.

According to one embodiment of the non-contact body temperature measuring device of the present invention, when the relative velocity is out of the predetermined velocity range, the processing unit controls the temperature measuring unit to stop measuring the temperatures of the plurality of measurement spots.

According to an embodiment of the non-contact body temperature measuring device of the present invention, the processing unit generates the body temperature measuring value based on an average value and a highest value of the temperatures of the plurality of measurement spots.

In order to achieve the objective, the present invention discloses a non-contact body temperature measuring method including steps of:

providing a non-contact body temperature measuring device including a temperature measuring unit, a Doppler radar, a processing unit and a display unit;

aligning the non-contact body temperature measuring device to a human body and moving the non-contact body temperature measuring device relative to the human body;

emitting a plurality of radar waves by the Doppler radar to the human body and receiving reflected radar waves reflected from the human body;

determining a plurality of measurement spots on the human body based on the reflected radar waves by the processing unit, and controlling the temperature measuring unit to measure temperatures of the plurality of measurement spots; and generating a body temperature measuring value based on the temperatures of the plurality of measurement spots by the processing unit.

In one embodiment, the non-contact body temperature measuring method further comprises a step of displaying the body temperature measuring value on the display unit.

According to an embodiment of the non-contact body temperature measuring method of the present invention, the non-contact body temperature measuring method further includes steps of:
  obtaining relative angles and relative distances between a plurality of locations on the human body and the Doppler radar based on the reflected radar waves by the processing unit; and
  determining the plurality of measurement spots based on the relative angle and the relative distance between the plurality of locations on the human body and the Doppler radar by the processing unit.

According to an embodiment of the non-contact body temperature measuring method of the present invention, the non-contact body temperature measuring method further includes steps of:
  obtaining a relative velocity between the human body and the Doppler radar based on the reflected radar waves by the processing unit; and
  generating the body temperature measuring value based on the temperatures of the plurality of measurement spots when the relative velocity is within a predetermined velocity range by the processing unit.

According to an embodiment of the non-contact body temperature measuring method of the present invention, the non-contact body temperature measuring method further includes a step of stopping the temperature measuring unit measuring the temperatures of the plurality of measurement spots when the relative velocity is out of the predetermined velocity range by the processing unit.

According to an embodiment of the non-contact body temperature measuring method of the present invention, the processing unit generates the body temperature measuring value based on an average value and a highest value of the temperatures of the plurality of measurement spots.

Compared with the conventional technology, the non-contact body temperature measuring device of the present invention comprises a Doppler radar arranged to determine the measurement spots having better angles and distances for performing temperature measurement. In addition, the non-contact body temperature measuring device of the present invention also determines whether the human body or the non-contact body temperature measuring device dramatically sways or quickly moves by means of the Doppler radar, so that the non-contact body temperature measuring device of the present invention can obtain a body temperature measuring value with higher accuracy.

BRIEF DESCRIPTION OF THE DRAWINGS

The structure, operating principle and effects of the present invention will be described in detail by way of various embodiments which are illustrated in the accompanying drawings.

DETAILED DESCRIPTION OF THE PREFERRED EMBODIMENT

Figure 1:
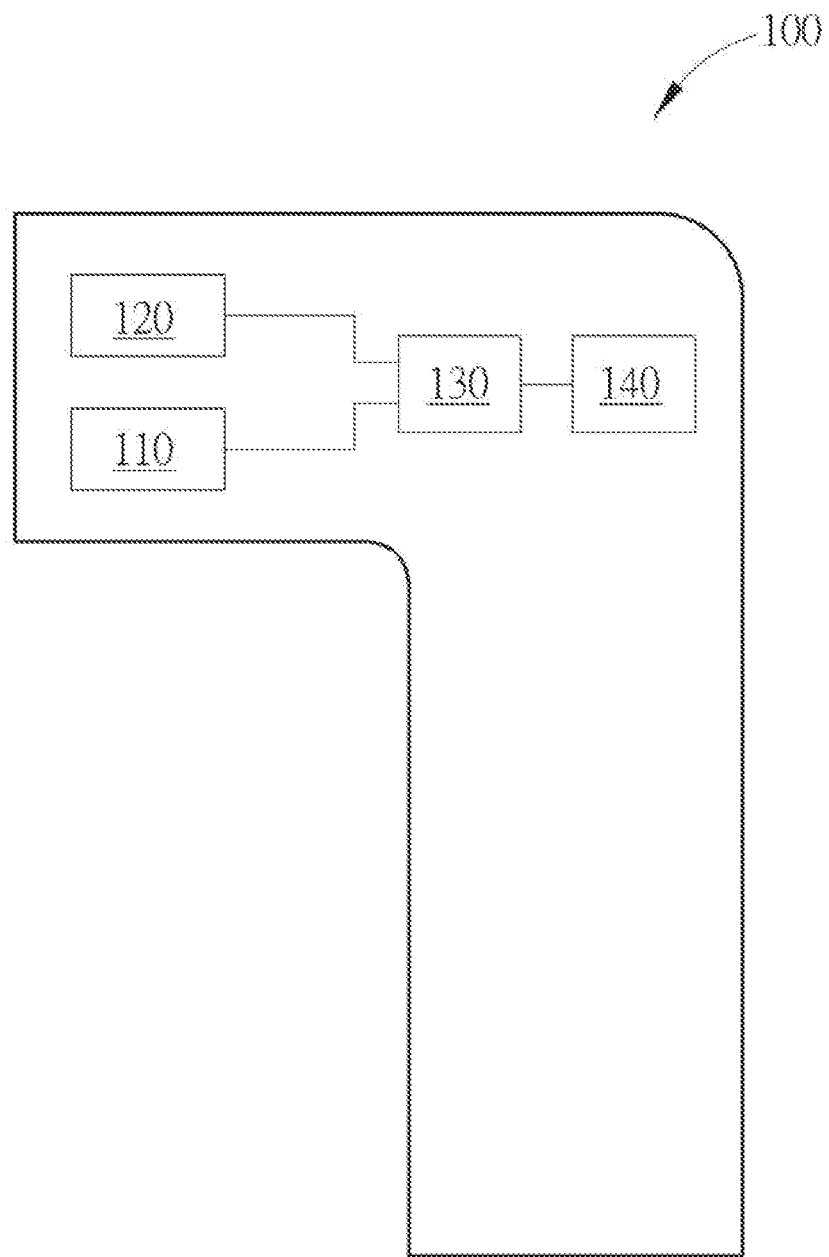
FIG. 1 is a schematic block diagram of a non-contact body temperature measuring device according to a preferred embodiment of the present invention.

The following embodiments of the present invention are herein described in detail with reference to the accompanying drawings. These drawings show specific examples of the embodiments of the present invention. These embodiments are provided so that this disclosure will be thorough and complete, and will fully convey the scope of the invention to those skilled in the art. It is to be acknowledged that these embodiments are exemplary implementations and are not to be construed as limiting the scope of the present invention in any way. Further modifications to the disclosed embodiments, as well as other embodiments, are also included within the scope of the appended claims.

These embodiments are provided so that this disclosure is thorough and complete, and fully conveys the inventive concept to those skilled in the art. Regarding the drawings, the relative proportions and ratios of elements in the drawings may be exaggerated or diminished in size for the sake of clarity and convenience. Such arbitrary proportions are only illustrative and not limiting in any way. The same reference numbers are used in the drawings and description to refer to the same or like parts. As used herein, the singular forms "a", "an" and "the" are intended to include the plural forms as well, unless the context clearly indicates otherwise.

It is to be acknowledged that, although the terms 'first', 'second', 'third', and so on, may be used herein to describe various elements, these elements should not be limited by these terms. These terms are used only for the purpose of distinguishing one component from another component. Thus, a first element discussed herein could be termed a second element without altering the description of the present disclosure. As used herein, the term "or" includes any and all combinations of one or more of the associated listed items.

It will be acknowledged that when an element or layer is referred to as being "on," "connected to" or "coupled to" another element or layer, it can be directly on, connected or coupled to the other element or layer, or intervening elements or layers may be present. In contrast, when an element is referred to as being "directly on," "directly connected to" or "directly coupled to" another element or layer, there are no intervening elements or layers present.

In addition, unless explicitly described to the contrary, the words "comprise" and "include", and variations such as "comprises", "comprising", "includes", or "including", will be acknowledged to imply the inclusion of stated elements but not the exclusion of any other elements.

Please referring to FIG. 1. a non-contact body temperature measuring device according to a preferred embodiment of the present invention is illustrated, wherein the non-contact body temperature measuring device 100 includes a temperature measuring unit 110, a Doppler radar 120, a processing unit 130, and a display unit 140. The temperature measuring unit 110 is configured to measure a temperature of a human body in a non-contact manner based on heat radiation of the human body. According to the preferred embodiment of the present invention, the temperature measuring unit 110 can be an infrared temperature measuring unit, but the present invention is not limited thereto. The Doppler radar 120 is arranged to emit a plurality of radar waves towards the human body and receive reflected radar waves reflected from the human body. The processing unit 130 is electrically connected to the temperature measuring unit 110 and the Doppler radar 120. The processing unit 130 controls the temperature measuring unit 110 to measure temperatures of a plurality of measurement spots on the human body based on the reflected radar waves received by the Doppler radar 120 and then generates a body temperature measuring value. The display unit 140 is electrically connected to the processing unit 130. The display unit 140 is configured to display the body temperature measuring value.

Figure 2:
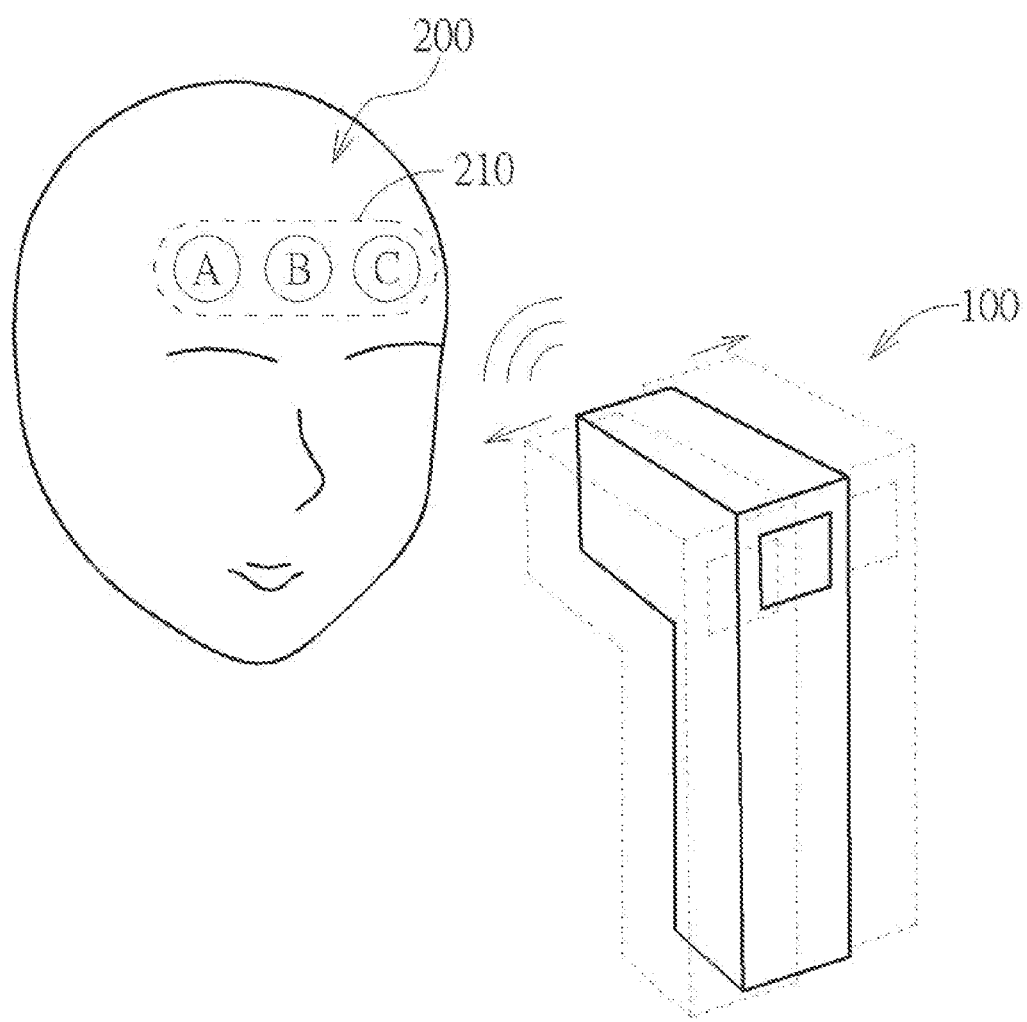
FIG. 2 is a schematic view illustrating an operation of the non-contact body temperature measuring device to measure body temperature according to the above preferred embodiment of the present invention.
Figure 3:
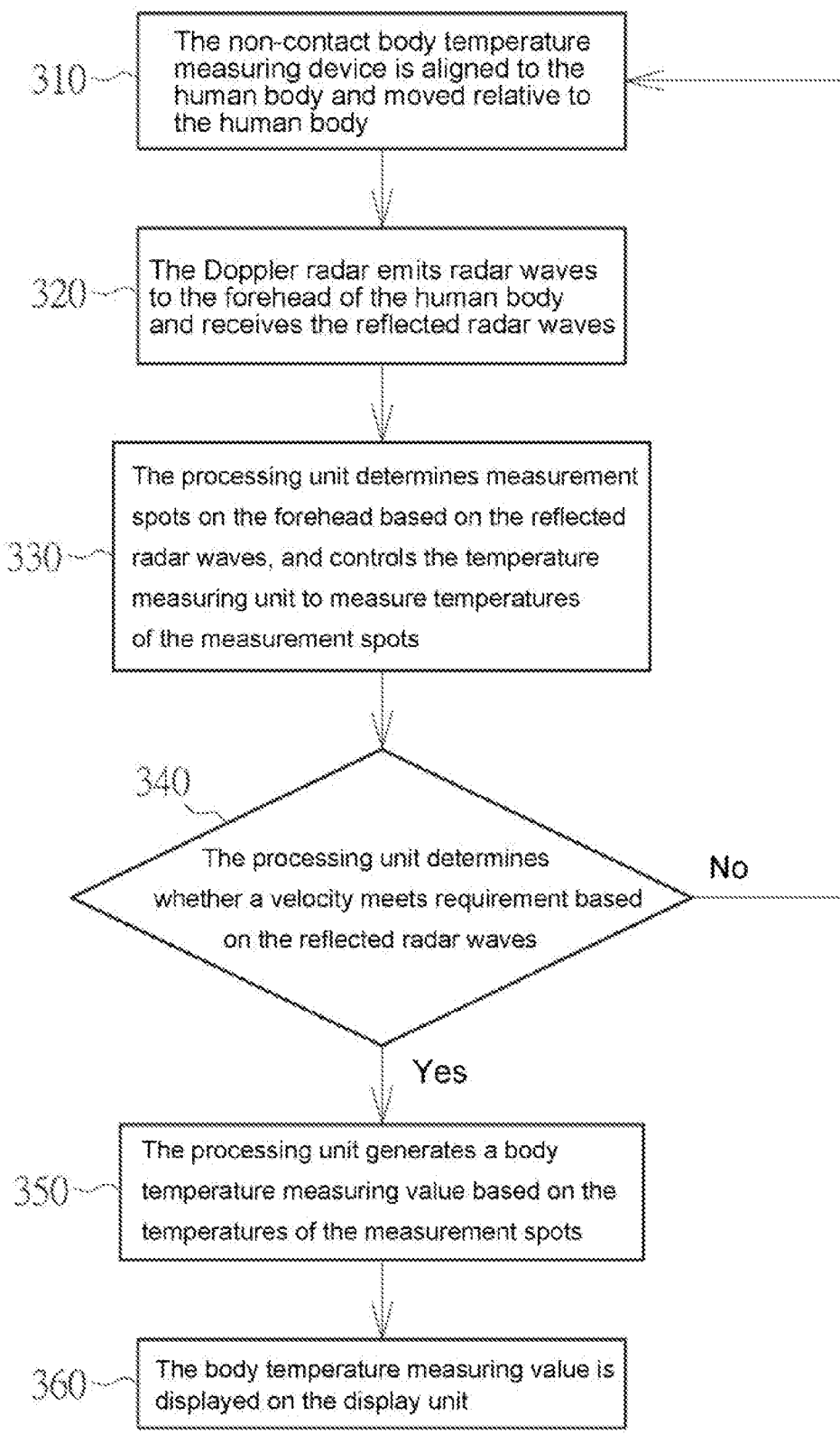
FIG. 3 is a flowchart of a non-contact body temperature measuring method according to the above preferred embodiment of the present invention.

Please refer to FIGS. 1 to 3. FIG. 2 is a schematic view illustrating an operation of the non-contact body temperature measuring device according to the preferred embodiment of the present invention to measure a body temperature. FIG. 3 is a flowchart of a non-contact body temperature measuring method according to the preferred embodiment of the present invention, comprising the following steps:

Step 310: Align the non-contact body temperature measuring device to a human body and move the non-contact body temperature measuring device relative to the human body.

Step 320: Emit radar waves from the Doppler radar to a forehead of the human body and receive reflected radar waves reflected from the human body.

Step 330: Determine measurement spots by the processing unit on the forehead based on the reflected radar waves and control the temperature measuring unit to measure temperatures of the measurement spots.

Step 340: Determine by the processing unit whether a velocity meets requirement based on the reflected radar waves.

Step 350: Generate a body temperature measuring value by the processing unit based on the temperatures of the measurement spots.

Step 360: Display the body temperature measuring value on the display unit.

In the step 310, after the non-contact body temperature measuring device 100 of the present invention is activated to measure the body temperature (for example, the temperature measuring button is pressed to start temperature measurement), the user can hold and align the non-contact body temperature measuring device 100 to the human body and move the non-contact body temperature measuring device 100 relative to the human body. For example, the user can hold and align the non-contact body temperature measuring device 100 to the forehead 200 of the human body and slowly move the non-contact body temperature measuring device 100 relative to the forehead 200 of the human body, so as to scan the forehead 200 of the human body.

In the step 320, during the scanning process, the Doppler radar 120 emits radar waves to the forehead 200 of the human body and receives the reflected radar waves.

In the step 330, the processing unit 130 determines a plurality of measurement spots on the forehead 200 based on the reflected radar waves, and controls the temperature measuring unit 110 to measure temperatures of the plurality of measurement spots. For example, the processing unit 130 can obtain relative angles and relative distances between a plurality of locations on a scanned area 210 of the forehead 200 and the Doppler radar 120 based on the energy values and the frequency difference of the reflected radar waves. It should be noted that the method of obtaining the relative angle and the relative distance based on the energy values and frequency difference of the reflected radar waves is a known technology, so the detailed description is not repeated herein. Next, the processing unit 130 determines the plurality of measurement spots (such as, measurement spots A, B, and C shown in FIG. 2) on the forehead 200 based on the relative angles and the relative distances between the plurality of locations on the scanned area 210 of the forehead 200 and the Doppler radar 120. In one embodiment, the relative angles between the surfaces of the measurement spots A, B, C and the Doppler radar 120 are within a preferred angle range, for example, the relative angle is closer to 90 degrees; and, the relative distances between the measurement spots A, B, C and the Doppler radar 120 are within a preferred distance range. After determining the plurality of measurement spots A, B and C on the forehead 200, the processing unit 130 controls the temperature measuring unit 110 to measure the temperatures of the plurality of measurement spots A, B, and C.

In the step 340, during the scanning process, the processing unit 130 determines whether a velocity meets requirement based on the reflected radar waves. For example, the processing unit 130 can obtain the relative velocity between the forehead 200 and the Doppler radar 120 based on the reflected radar waves, and then determine whether the relative velocity between the forehead 200 and the Doppler radar 120 is within a predetermined velocity range.

In the step 350, when the processing unit 130 determines that the relative velocity is within the predetermined velocity range, it indicates that the forehead 200 or the non-contact body temperature measuring device 100 does not dramatically sway or quickly move, the temperature measuring unit 110 can measure a temperature with higher accuracy, so the processing unit 130 generates a body temperature measuring value based on the temperatures of the plurality of measurement spots A, B, and C. When the processing unit 130 determines that the relative velocity is out of the predetermined velocity range, it indicates that the forehead 200 or the non-contact body temperature measuring device 100 dramatically sways or quickly moves, and the temperature measured by the temperature measuring unit 110 may be inaccurate, so the processing unit 130 does not generate the body temperature measuring value, and the non-contact body temperature measuring method executes the scanning operation on the forehead 200 of the human body again, that is, the step 310 is executed again.

In the step 360, after the processing unit 130 generates the body temperature measuring value, and the body temperature measuring value is displayed on the display unit 140.

It is worth mentioning that in the non-contact body temperature measuring method according to the preferred embodiment of the present invention, the above-mentioned steps are not limited to be executed in the aforementioned order; in other words, the execution order of the above-mentioned steps can be changed, and another step can be intervened between the above-mentioned steps.

According to aforementioned configuration, the non-contact body temperature measuring device 100 of the present invention utilizes the Doppler radar 120 to determine better angles and distances of the measurement spots, so as to measure the temperatures with higher accuracy. The non-contact body temperature measuring device 100 of the present invention further uses the Doppler radar 120 to determine whether the human body or the non-contact body temperature measuring device 100 dramatically sways or quickly moves, so as to reduce measurement error.

Furthermore, according to the preferred embodiment of the present invention, the processing unit 130 generates the body temperature measuring value based on an average value and a highest value of the temperatures of the plurality of measurement spots A, B and C, but the present invention is not limited thereto. For example, the processing unit 130 obtains the average value and the highest value of the temperatures of the plurality of measurement spots A, B, and C first, and when the difference between the highest value and the average is not high enough, the processing unit 130 can use the highest value as the body temperature measuring value. In an alternative mode of the preferred embodiment of the present invention, the processing unit 130 can generate the body temperature measuring value based on another static value of the temperatures of the plurality of measurement spots A, B and C. Furthermore, the amount of the measurement spots described in the embodiment of the present invention is an example, the non-contact body temperature measuring device 100 of the present invention can measure the temperatures of more than 3 measurement spots, so as to obtain the body temperature measuring value with higher accuracy.

On the other hand, the non-contact body temperature measuring device 100 of the present invention is not limited to measure the temperature of the forehead 200 of the human body; for example, the non-contact body temperature measuring device 100 of the present invention can be used to measure the temperature of other part of the human body.

Compared with the conventional technology, the non-contact body temperature measuring device of the present invention uses the Doppler radar to determine the measurement spot having better angle and distance for performing temperature measurement, and to determine whether the human body or the non-contact body temperature measuring device dramatically sways or quickly moves, so that the non-contact body temperature measuring device 100 of the present invention can obtain the body temperature measuring value with higher accuracy.

The present invention disclosed herein has been described by means of specific embodiments. However, numerous modifications, variations and enhancements can be made thereto by those skilled in the art without departing from the spirit and scope of the disclosure set forth in the claims.

What is claimed is:

1. A non-contact body temperature measuring device for measuring a temperature of a human body, comprising:
a temperature measuring unit configured for measuring the temperature of the human body in a non-contact manner;
a Doppler radar configured to emit a plurality of radar waves towards the human body, and receive reflected radar waves reflected from the human body; and
a processing unit, which is electrically connected to the temperature measuring unit and the Doppler radar, being configured to determine a plurality of measurement spots on the human body based on the reflected radar waves, control the temperature measuring unit to measure temperatures of the plurality of measurement spots, and generate a body temperature measuring value based on the temperatures of the plurality of measurement spots;
wherein the processing unit is configured to obtain relative angles and relative distances between a plurality of locations on the human body and the Doppler radar based on the reflected radar waves, and to determine the plurality of measurement spots on the human body based on the relative angles and the relative distances between the plurality of locations and the Doppler radar.

2. The non-contact body temperature measuring device according to claim 1, further comprising a display unit electrically connected to the processing unit and configured to display the body temperature measuring value.

3. The non-contact body temperature measuring device according to claim 1, wherein the temperature measuring unit is an infrared temperature measuring unit.

4. The non-contact body temperature measuring device according to claim 1, wherein the processing unit is configured to obtain a relative velocity between the human body and the Doppler radar based on the reflected radar waves, wherein when the relative velocity is within a predetermined velocity range, the processing unit generates the body temperature measuring value based on the temperatures of the plurality of measurement spots.

5. The non-contact body temperature measuring device according to claim 4, wherein when the relative velocity is out of the predetermined velocity range, the processing unit does not generate the body temperature measuring value.

6. The non-contact body temperature measuring device according to claim 1, wherein the processing unit generates the body temperature measuring value based on an average and a highest value of the temperatures of the plurality of measurement spots.

7. A non-contact body temperature measuring method, comprising:
providing a non-contact body temperature measuring device which includes a temperature measuring unit, a Doppler radar and a processing unit;
aligning the non-contact body temperature measuring device to a human body and moving the non-contact body temperature measuring device relative to the human body;
emitting a plurality of radar waves by the Doppler radar to the human body, and receiving reflected radar waves reflected from the human body;
obtaining relative angles and relative distances between a plurality of locations on the human body and the Doppler radar by the processing unit based on the reflected radar waves;
determining the plurality of measurement spots by the processing unit based on the relative angle and the relative distance between the plurality of locations on the human body and the Doppler radar;
controlling the temperature measuring unit to measure temperatures of the plurality of measurement spots; and
generating a body temperature measuring value based on the temperatures of the plurality of measurement spots by the processing unit.

8. The non-contact body temperature measuring method according to claim 7, further comprising:
obtaining a relative velocity between the human body and the Doppler radar based on the reflected radar waves by the processing unit; and
generating the body temperature measuring value by the processing unit based on the temperatures of the plurality of measurement spots when the relative velocity is within a predetermined velocity range.

9. The non-contact body temperature measuring method according to claim 8, further comprising:
controlling the processing unit to not generate the body temperature measuring value when the relative velocity is out of the predetermined velocity range.

10. The non-contact body temperature measuring method according to claim 7, wherein the processing unit generates the body temperature measuring value based on an average value and a highest value of the temperatures of the plurality of measurement spots.

11. The non-contact body temperature measuring method according to claim 7, further comprising displaying the body temperature measuring value on a display unit of the non-contact body temperature measuring device.

12. The non-contact body temperature measuring method according to claim 7, further comprising displaying the body temperature measuring value on a display unit of the non-contact body temperature measuring device.

13. The non-contact body temperature measuring method according to claim 8, further comprising displaying the body temperature measuring value on a display unit of the non-contact body temperature measuring device.

14. The non-contact body temperature measuring method according to claim 9, further comprising displaying the body temperature measuring value on a display unit of the non-contact body temperature measuring device.

15. The non-contact body temperature measuring method according to claim 10, further comprising displaying the body temperature measuring value on a display unit of the non-contact body temperature measuring device.

* * * * *